United States Patent
Potthast et al.

[11] Patent Number: 5,624,640
[45] Date of Patent: Apr. 29, 1997

[54] SENSOR FOR DETECTING NITROGEN OXIDE

[75] Inventors: Heidrun Potthast, Korntal-Muenchingen; Bernd Schumann, Rutesheim, both of Germany

[73] Assignee: Robert Bosch GmbH, Stuttgart, Germany

[21] Appl. No.: 628,664

[22] PCT Filed: Sep. 14, 1994

[86] PCT No.: PCT/DE94/01051

§ 371 Date: Apr. 12, 1996

§ 102(e) Date: Apr. 12, 1996

[87] PCT Pub. No.: WO95/10774

PCT Pub. Date: Apr. 20, 1995

[30] Foreign Application Priority Data

Oct. 12, 1993 [DE] Germany .................. 43 34 672.3

[51] Int. Cl.⁶ .................................................. G01N 27/12
[52] U.S. Cl. ........................ 422/90; 422/98; 436/116; 204/432; 338/34
[58] Field of Search ................ 422/90, 98; 436/116, 436/117, 118; 204/424, 429, 432; 324/71.5; 338/34

[56] References Cited

U.S. PATENT DOCUMENTS

| | | |
|---|---|---|
| 3,695,848 | 10/1972 | Taguchi . |
| 3,699,803 | 10/1972 | Sumi et al. . |
| 4,722,905 | 2/1988 | Honeybourne et al. ............. 436/151 |
| 4,840,913 | 6/1989 | Logothetis et al. ................. 436/116 |
| 5,314,828 | 5/1994 | Dalla Betta et al. ................ 436/118 |
| 5,358,874 | 10/1994 | Tsurumi ............................. 436/116 |

FOREIGN PATENT DOCUMENTS

| | | |
|---|---|---|
| 0517366 | 12/1992 | European Pat. Off. . |
| 2648373 | 4/1978 | Germany . |
| 2937802C2 | 2/1987 | Germany . |
| 3802052A1 | 8/1988 | Germany . |

OTHER PUBLICATIONS

Journal of Materials Science, vol. 25, No. 5, May 1990, London, Great Britain, pp. 2632–2636; Y. Sadaoka et al "Effect of NO2 in air on the electrical conductance of In2O3 films with and without added ZnO . . . Sputtering".

Primary Examiner—Jeffrey Snay
Attorney, Agent, or Firm—Spencer & Frank

[57] ABSTRACT

A sensor is proposed for detecting nitrogen oxides (NO, $NO_2$, $N_2O_4$) in a test gas, having a semiconducting metal oxide layer (3) which is deposited on a ceramic substrate (10) and whose electrical resistance provides information about the concentration of nitrogen oxides (NO, $NO_2$, $N_2O_4$) in the test gas. The main components of the sensor are a converter layer (4) which is deposited on the metal oxide layer (3) and is made of a material which causes the oxidation of combustible components of the test gas and converts the nitrogen monoxide (NO) contained in the test gas into nitrogen dioxide ($NO_2$) or dinitrogen tetroxide ($N_2O_4$), which then reaches the metal oxide layer (3), as well as a heating device (5) which heats the metal oxide layer (3) and the converter layer (4). The converter layer is suitably constituted of titanium oxide ($TiO_2$) and/or zirconium oxide ($ZrO_2$) and/or silicon oxide ($SiO_2$) and/or aluminum oxide ($Al_2O_3$) and has a platinum content of from 0.01 to 20 weight percent.

13 Claims, 2 Drawing Sheets

SENSOR FOR DETECTING NITROGEN OXIDE

PRIOR ART

The invention relates to a sensor for detecting nitrogen oxides (NO, $NO_2$, $N_2O_4$) as generically defined by the preamble to claim 1. For determining specific components of a test gas, the use of sensors has been disclosed whose sensitive element is a semiconductor material whose electrical resistance changes when in contact with the specific gas components. This kind of sensor is used in particular to determine the oxygen content in exhaust gasses, for example from internal combustion engines, but is also used to determine methane, carbon monoxide, or alcohol content. In particular, semiconducting metal oxides such as tin oxide ($SnO_2$), zinc oxide (ZnO), titanium oxide ($TiO_2$), or tungsten oxide ($WO_3$) are used as the semiconducting materials, depending upon the purpose.

These known gas sensors are usually manufactured using thick-film or thin-film technology. Strip conductors, by means of which the resistance change is later measured, as well as the semiconducting oxide, are deposited on an insulating, preferably ceramic substrate, for example of aluminum oxide ($Al_2O_3$). In order on the one hand to increase the sensitivity of the sensor—this depends on temperature—and on the other hand to assure the maintenance of the dynamic equilibrium of adsorption and desorption, it is customary to heat the substrate with the sensor device. Heating devices required for this can be disposed according to known proposed embodiments, for example on the underside of the substrate—if the sensor device is mounted on the top side—, or they can be integrated into the substrate, or be disposed between the substrate surface and the sensor device.

For example, EP-OS 313 390 discloses a sensor of this kind. In the sensor described there, the heating device and sensor device are disposed on one side of a substrate of aluminum oxide ($Al_2O_3$). Tin oxide ($SnO_2$) is proposed as the semiconducting material to detect methane gas, tungsten oxide ($WO_3$) for detecting carbon monoxide, or lanthanum nickel oxide ($LaNiO_3$) for detecting alcohol.

DE-OS 36 24 217 discloses a sensor in which the heating device is integrated into the substrate. Once again aluminum oxide ($Al_2O_3$) is suggested as the material for the substrate, the gas-sensitive semiconductor layer in this case is comprised of porous titanium oxide ($TiO_2$) which is enriched with another metal oxide. The described sensor is provided in particular for regulating the fuel/air ratio in an exhaust gas by measuring the oxygen content.

Although these known sensors based on semiconducting oxides have proven to be practical for detecting CO, $H_2$, and hydrocarbons, they are unsuited for detecting nitrogen monoxide (NO) or nitrogen dioxide ($NO_2$). However, their detection in particular is of considerable significance for the verification of diesel exhaust gasses. These contain primarily nitrogen monoxide (NO), which is converted in minutes almost completely into nitrogen dioxide ($NO_2$) or dinitrogen tetroxide ($N_2O_4$). Because of the different effects of nitrogen monoxide (NO) or nitrogen dioxide ($NO_2$) on the semiconducting oxide, this reacts with a complex resistance behavior, which cannot be suitably evaluated. The use of phthalocyanine layers, which detect $NO_x$ molecules contained in the exhaust, is therefore known for the verification of diesel exhaust gasses. For example, the verification of diesel exhaust gasses can in turn be used to interrupt the supply of external air, in which diesel exhaust gasses have been detected, to rooms or vehicles by means of a control flap in ventilators or air conditioners. The precise knowledge of the percentage of nitrogen oxides (NO, $NO_2$, ...) in exhaust gases is of particular interest for monitoring and regulating internal combustion engines or furnaces. This particularly applies if catalysts and other processes are used to optimize combustion and reduce undesirable exhaust gas components such as NO, CO, or hydrocarbons.

The object of the instant invention is to disclose a sensor and a process for producing it, which is designed simply and permits a sufficiently favorable determination of the percentage of nitrogen oxides in a test gas.

This object is attained by a sensor or a process with the characteristics of claim 1. The sensor according to the invention can be produced by means of fundamentally known techniques and is therefore cost-effective in manufacturing. In use it indicates nitrogen oxide-containing gasses rapidly and with favorable sensitivity, without being affected at the same time by CO, $H_2$, or $CH_x$ components that are present. It is therefore particularly suited for use in motor vehicles for controlling the interior ventilation, which it interrupts if necessary when diesel exhaust gasses penetrate into the interior.

Advantageous improvements and suitable embodiments of the sensor according to the invention or the process for its production ensue from the dependent claims.

By coating the sensor with palladium (Pd), the nitrogen oxide ($NO_2$) sensitivity can be adjusted with a view to the predetermined employment. A second coating of the sensor with platinum (Pt) and/or rhodium (Rh) is suitably employed to support the desorption of the nitrogen dioxide ($NO_2$) produced as well as to improve the rate of increase and differentiation of the signal when there are different nitrogen dioxide ($NO_2$) concentrations. As a result, the sensor can detect low concentrations of NO/$NO_2$ which are normal in street traffic with a stable basic resistance, without leading to a continuous increase of the resistance and drift.

It is furthermore advantageous that, in contrast to organic phthalocyanine sensors, for example, the proposed sensor can be heated up to temperatures of 700° C. to periodically clean it and to stabilize the surfaces.

The proposed sensor is also favorably suited to generally determine the NO/$NO_2$ content in the exhaust gas of heating systems as a function of its oxygen content.

The proposed sensor is will be explained in detail below by means of exemplary embodiments shown in the drawings.

Figure 5:
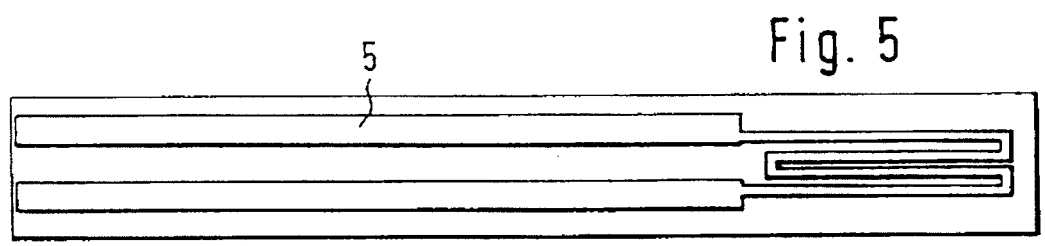
Figure 6:
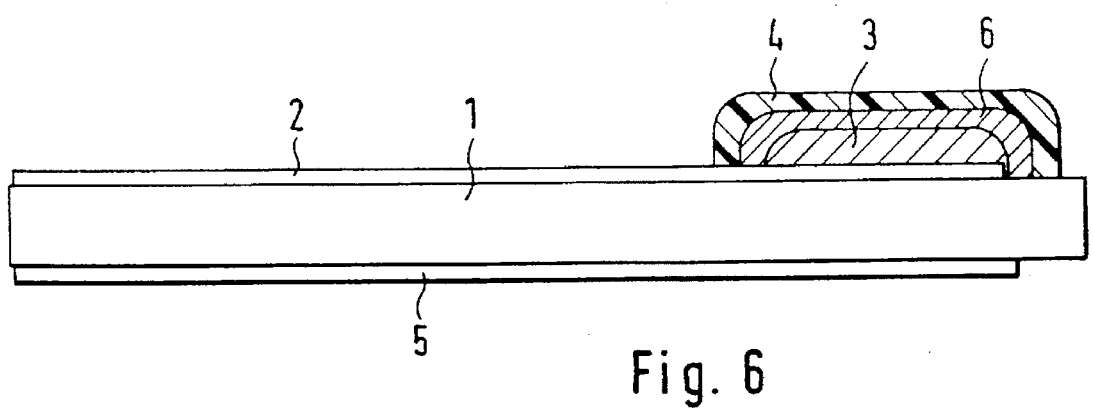

FIG. 5. shows a bottom view of the same sensor,

FIG. 6 shows a lateral view of another embodiment of the sensor, and

Figure 7:
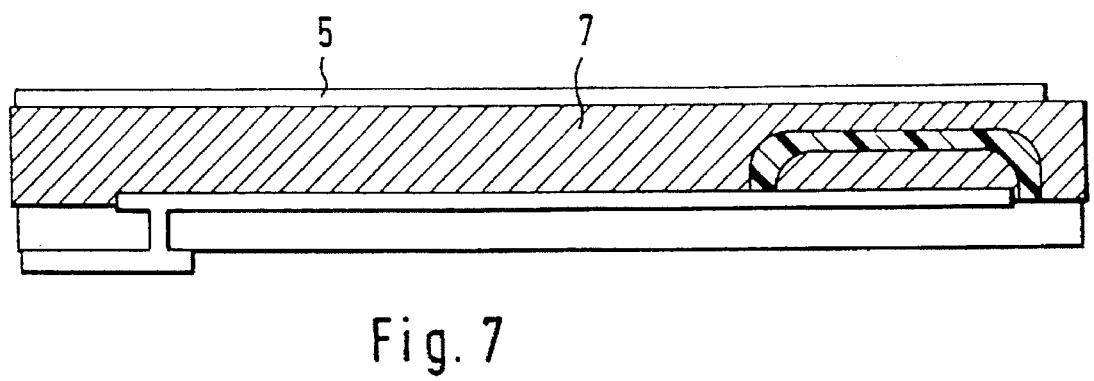

FIG. 7 shows a lateral view of another embodiment of the sensor with an intermediate layer disposed over the sensitive semiconductor layer.

Figure 1:
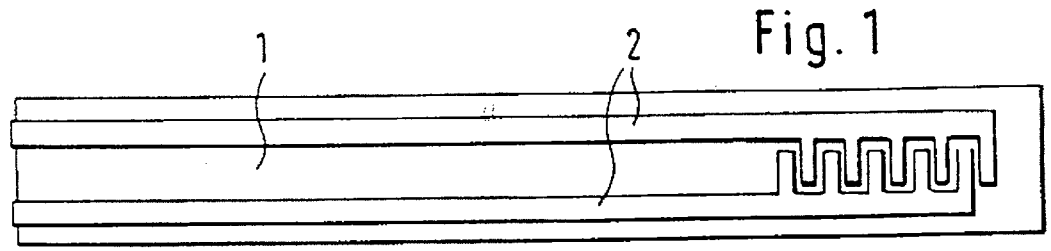
FIGS. 1 to 3 show top views of a sensor according to the invention.

FIG. 1 shows a top view of a proposed sensor which was embodied in the shape of a rod. It is comprised of a substrate of an electrically insulating and heat resistant material, preferably aluminum oxide ($Al_2O_3$), to which the other components which make up the sensor are deposited using thick-film technology. On a surface of the substrate, which is indicated here as the top, two strip conductors 2 are mounted, which interlock with each other in comb fashion on their head ends.

A semiconducting metal oxide layer 3 of a thickness of 10 to 500 μm is suitably deposited over the strip conductors in the area of the interlocking ends. It is comprised of diindium trioxide ($In_2O_3$) or tin oxide ($SnO_2$), to which a conductivity-increasing doping element is added in concentrations of from 0.005 to 0.05 mol/%. Tantalum (Ta), niobium (Nb), antimony (Sb), or tungsten (W) can be used as a doping element, with indium oxide ($In_2O_3$) also tin (Sn), titanium (Ti), or cerium (Ce). To limit the growth of crystallite, and thereby to increase the sensitivity and to improve the longevity of the sensors, a bivalent element, in particular magnesium (Mg), barium (Ba), calcium (Ca), strontium (Sr), zinc (Zn), or a trivalent element such as aluminum oxide ($Al_2O_3$) can be additionally contained in the metal oxide in concentrations of 0.001 to 45. The metal oxide of the layer 3 is furthermore impregnated with a noble metal additive. This is comprised in particular of palladium (Pd) with additions of platinum (Pt) and/or rhodium (Rh) in a concentration of from 0.001 to 5 mol %. In this case the palladium (Pd) is used to adjust the nitrogen dioxide ($NO_2$) sensitivity. The platinum or rhodium addition makes it easier to desorb the nitrogen dioxide ($NO_2$) produced. Furthermore, it improves the rate of increase as well as the differentiation of the signal when there are different nitrogen dioxide ($NO_2$) concentrations. As a result, the sensor can detect low concentrations of nitrogen oxide/nitrogen dioxide which are normal in street traffic with a stable base resistance, without leading to a continuous increase of the resistance and to drift.

Figure 2:
Figure 3:
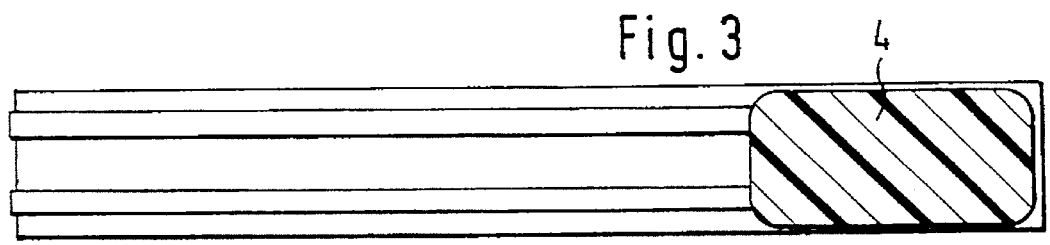
Figure 4:
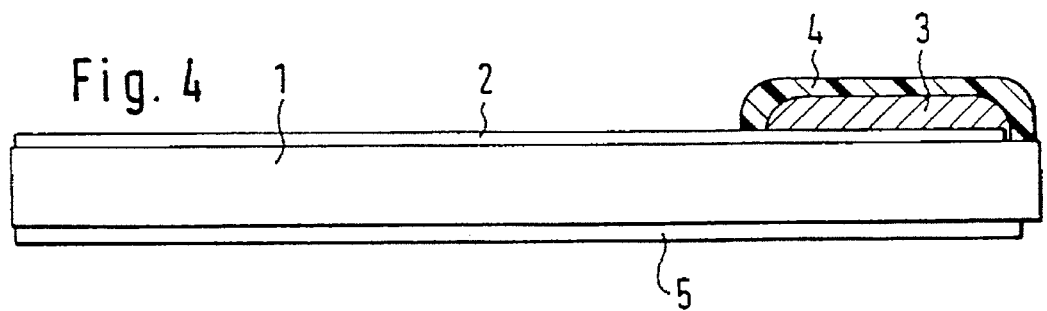
FIG. 4 shows a lateral view of the same sensor.

A converter layer 4 is deposited at a suitable thickness of 10 to 100 μm over the metal oxide layer 3. It is preferably comprised of aluminum oxide ($Al_2O_3$), titanium oxide ($TiO_2$), zirconium oxide ($ZrO_2$), or silicon oxide ($SiO_2$) with a platinum content of from 0.01 to 20%. Its production is based on a powdery starting material, which is impregnated with the platinum or with the noble metal used, or which is added to the platinum-containing metal powder. A heating device 5 is disposed on the opposite side of the substrate 1, which is indicated here as the underside according to the representations in FIGS. 1 to 3, and is shown in a top view in FIG. 5. It is comprised essentially of a meandering strip conductor in the area beneath the metal oxide layer 3.

The principal function of the sensor according to the invention is first to convert nitrogen oxide contained in the test gas into nitrogen dioxide ($NO_2$) and then to supply this to the sensitive metal oxide layer 3. The conversion is carried out in the converter layer 4 using atmospheric oxygen to oxidize the nitrogen monoxide (NO) into nitrogen dioxide ($NO_2$) or dinitrogen tetroxide ($N_2O_4$). The converter layer 4 simultaneously fulfills the function of keeping the nitrogen monoxide (NO), which has not yet been converted, away from the semiconducting metal oxide layer 3. Its thickness must be appropriately selected so that no nitrogen monoxide (NO) reaches the metal oxide layer. The converter layer 4 is furthermore used to oxidize combustible components contained in the test gas, such as carbon monoxide (CO), hydrogen ($H_2$), or hydrocarbons, using the oxygen contained in the test gas. As a result, combustible and/or oxidizable components of the test gas no longer affect the electrical properties of the semiconducting metal oxide and hence no longer affect the measurement result. The converter layer 4 fulfills a further function by storing the nitrogen monoxide (NO) or nitrogen dioxide ($NO_2$) up to a quantity determined by the retention time of the gas molecules via the semiconducting metal oxide layer 3. As a result, when there are low concentrations of nitrogen monoxide (NO), the sensitivity of the sensor increases as more NO is converted into $NO_2$.

The nitrogen dioxide ($NO_2$) reaching the n-conducting metal oxide layer 3 binds electrons on contact with the surface because of its dipole properties and thus causes an increase of the electrical resistance of the metal oxide layer 3, which is measured in a known manner. In addition, a constant current is applied, for example via the conductor strips 2; the changes of the voltage required for maintaining the constant current following the change of the resistance of the metal oxide layer 3 are measured.

In order to increase the sensitivity of the sensor 1 to 4, it is heated from the underside of the substrate 1 to a temperature of approximately 180° to 400° C. by means of the heating device 5. As a result of the heating, the conductivity in the metal oxide layer 3 increases. Furthermore, the heating supports the maintenance of the dynamic equilibrium of adsorption and desorption. In addition, it accelerates the oxidation of the combustible components contained in the test gas.

FIG. 6 shows another embodiment of the sensor according to the invention. It differs from the variants shown in FIGS. 1 to 5 in the fact that another intermediate converter layer 6 has been inserted between the metal oxide layer 3 and converter layer 4. Like the first converter layer 4, it is comprised, for example, of aluminum oxide ($Al_2O_3$), titanium oxide ($TiO_2$), zirconium oxide ($ZrO_2$), or silicon oxide ($SiO_2$), but preferably has a reduced noble metal content, such as of platinum, of from 0.001 to 2%. Its thickness suitably is between 10 and 500 μm. In order to adapt the adhesion and thermal expansion of the intermediate converter layer 6 to that of the metal oxide layer 3, mixtures of the mentioned oxides with tin oxide ($SnO_2$) or diindium trioxide ($In_2O_3$) can also be used.

The intermediate converter layer 6 additionally assures that all nitrogen monoxide (NO) is converted into nitrogen dioxide ($NO_2$) or dinitrogen tetroxide ($N_2O_4$), and no nitrogen monoxide (NO) reaches the metal oxide layer 3. The retention time of the nitrogen monoxide (NO) or nitrogen dioxide ($NO_2$) molecules is increased by the metal oxide layer 3. The insertion of the intermediate converter layer 6 leads to a separation of function in such a way that the oxidation of combustible components of the test gas essentially occurs in the converter layer 4, while the conversion of nitrogen monoxide (NO) takes place in the intermediate converter layer 6. A construction with two converter layers 4 or 6 is therefore advised, particularly when there are high concentrations of combustible components in the test gas.

Both the intermediate converter layer 6 and the converter layer 4 can contain other components for accelerating the oxidation processes, such as cerium oxide ($CeO_2$).

The exemplary embodiment according to FIG. 5 demonstrates another possibility for the disposition of the heating device 5. A porous layer 7, for example of aluminum oxide ($Al_2O_3$) and/or glass powder of a thickness of 100 to 500 μm, is deposited over the sensor layer device 1 to 4. The heating device 5 is placed on the top of the porous layer 7 which in this way heats the sensor device 1 to 4 from the top. A pore forming material is suitably added to at least one converter layer 4 or 6 so that the temperature of the metal oxide layer 3 can be kept lower than the temperature of the converter layer 4 or 6. A device according to FIG. 5 permits the operation of the sensor at temperatures of up to 450° C.

We claim:

1. A sensor for detecting nitrogen oxides (NO, $NO_2$, $N_2O_4$) in a test gas, the sensor having with a semiconducting metal oxide layer, which is deposited on a substrate and whose electrical resistance varies in relation to the concentration of nitrogen oxides (NO, $NO_2$, $N_2O_4$) in the test gas, the sensor having a converter layer which is deposited on the metal oxide layer and is made of a material which causes the oxidation of combustible components of the test gas and converts the nitrogen monoxide (NO) contained in the test gas into nitrogen dioxide ($NO_2$) or dinitrogen tetroxide ($N_2O_4$), which then reaches the metal oxide layer, said converter layer having a first layer and an intermediate second layer each of said first and second layers having a ceramic base material and to each of which first and second layers there is added a catalytically effective percentage of noble metal(s) of the platinum group in concentrations which differ from each other, the sensor further having a heating device which heats the metal oxide layer and the converter layer.

2. The sensor according to claim 1, wherein the ceramic base material of the converter layers includes one or more materials selected from titanium oxide ($TiO_2$), zirconium oxide ($ZrO_2$), silicon oxide ($SiO_2$), and aluminum oxide ($Al_2O_3$).

3. A sensor according to claim 1, wherein said intermediate second layer contains from 0.001 to 2 weight percent of noble metal.

4. A sensor according to claim 1, wherein said metal oxide layer (3) contains palladium (Pd) with an addition of platinum (Pt), rhodium (Rh), an alloy thereof in a concentration of from 0.001 to 5 mol %.

5. A sensor according to claim 1, wherein a porous layer is provided on said converter layer, said heating device being arranged on the upper surface of said porous layer.

6. A sensor as defined in claim 1 wherein said first layer contains from 0.01 to 20 weight percent of noble metal.

7. A sensor according to claim 6, wherein said noble metal includes one or more metals selected from platinum (Pt), Rhodium (Rh), palladium (Pd) and an alloy of the foregoing.

8. A sensor according to claim 1, wherein said metal oxide layer is comprised of a semiconductor metal oxide into which there is mixed a conductivity-increasing doping element in a concentration of from $5 \times 10^{-4}$ to $5 \times 10^{-2}$ mol %.

9. A sensor according to claim 8, wherein said semiconductor metal oxide is indium oxide ($In_2O_3$) or tin oxide ($SnO_2$).

10. A sensor according to claim 8, wherein said doping element is tantalum (Ta), niobium (Nb), antimony (Sb) or tungsten (W).

11. A sensor according to claim 8, wherein said semiconductor metal oxide is indium oxide ($In_2O_3$) and said doping element is tin (Sn), titanium (Ti) or cerium (Ce).

12. A sensor according to claim 1, wherein said metal oxide layer additionally contains one or more elements selected from a two-valent element of the main group II, a three-valent element of the main group III, a three-valent element of the rare earths, as an oxide, in a concentration of from 000.1 to 45 weight percent.

13. A sensor according to claim 12, wherein said additional element is magnesium (Mg), barium (Ba), calcium (Ca, strontium (Sr), zinc (Zn) or aluminum oxide ($Al_2O_3$).

* * * * *